US006899106B1

United States Patent
Al-Killidar

(12) 
(10) Patent No.: US 6,899,106 B1
(45) Date of Patent: May 31, 2005

(54) APPARATUS FOR PRODUCING A HEMATOMA

(76) Inventor: Adnan Al-Killidar, 215 Edgeware Road, London W2-1ES (GB)

( * ) Notice: Subject to any disclaimer, the term of this patent is extended or adjusted under 35 U.S.C. 154(b) by 0 days.

(21) Appl. No.: 09/865,352

(22) Filed: May 25, 2001

(51) Int. Cl.[7] ............................................... A61B 19/00
(52) U.S. Cl. ............................ 128/898; 128/897; 601/6; 601/14; 601/12
(58) Field of Search ................................ 128/897, 898; 601/6, 14, 12, 10

(56) References Cited

U.S. PATENT DOCUMENTS

| 75,412 A | 3/1868 | Hadfield |
| 843,674 A | 2/1907 | Funk |
| 5,149,331 A | 9/1992 | Ferdman et al. |
| D340,181 S | 10/1993 | Adams et al. |
| 5,320,607 A | 6/1994 | Ishibashi |
| 5,636,643 A | 6/1997 | Argenta et al. |
| 5,680,872 A | 10/1997 | Sesekura et al. |
| 6,277,052 B1 * | 8/2001 | Howard .......................... 482/4 |
| 6,319,211 B1 * | 11/2001 | Ito et al. ........................ 601/7 |

* cited by examiner

*Primary Examiner*—Teresa Walberg
*Assistant Examiner*—Shawntina T. Fuqua

(57) ABSTRACT

An apparatus for producing a hematoma for encouraging the increased production of hemoglobin. The apparatus for producing a hematoma includes a pressure bell having a wall defining an interior space and a lip extending around a lower periphery of the wall designed for providing a substantially airtight seal against a skin of a user, a housing removably coupled to and in fluid communication with an insertion port of the pressure bell, and a vacuum assembly positioned within the housing for removing air from the interior space of the pressure bell such that a lower pressure area is created within the pressure bell thereby drawing blood to a surface of the skin of the user.

13 Claims, 3 Drawing Sheets

APPARATUS FOR PRODUCING A HEMATOMA

BACKGROUND OF THE INVENTION

1. Field of the Invention

The present invention relates to localized negative pressure devices and more particularly pertains to a new apparatus for producing a hematoma for encouraging the increased production of hemoglobin.

2. Description of the Prior Art

The use of localized negative pressure devices is known in the prior art. More specifically, localized negative pressure devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,149,331; U.S. Pat. No. 5,636,643; U.S. Pat. No. Des. 340,181; U.S. Pat. No. 75,412; U.S. Pat. No. 843,674; U.S. Pat. No. 5,320,607; and U.S. Pat. No. 5,680,871.

While these devices fulfill their respective, particular objectives and requirements, the aforementioned patents do not disclose a new apparatus for producing a hematoma. The inventive device includes a pressure bell having a wall defining an interior space and a lip extending around a lower periphery of the wall designed for providing a substantially airtight seal against a skin of a user, a housing removably coupled to and in fluid communication with an insertion port of the pressure bell, and a vacuum assembly positioned within the housing for removing air from the interior space of the pressure bell such that a lower pressure area is created within the pressure bell thereby drawing blood to a surface of the skin of the user.

In these respects, the apparatus for producing a hematoma according to the present invention substantially departs from the conventional concepts and designs of the prior art, and in so doing provides an apparatus primarily developed for the purpose of encouraging the increased production of hemoglobin.

SUMMARY OF THE INVENTION

In view of the foregoing disadvantages inherent in the known types of localized negative pressure devices now present in the prior art, the present invention provides a new apparatus for producing a hematoma construction wherein the same can be utilized for encouraging the increased production of hemoglobin.

The general purpose of the present invention, which will be described subsequently in greater detail, is to provide a new apparatus for producing a hematoma apparatus and method which has many of the advantages of the localized negative pressure devices mentioned heretofore and many novel features that result in a new apparatus for producing a hematoma which is not anticipated, rendered obvious, suggested, or even implied by any of the prior art localized negative pressure devices, either alone or in any combination thereof.

To attain this, the present invention generally comprises a pressure bell having a wall defining an interior space and a lip extending around a lower periphery of the wall designed for providing a substantially airtight seal against a skin of a user, a housing removably coupled to and in fluid communication with an insertion port of the pressure bell, and a vacuum assembly positioned within the housing for removing air from the interior space of the pressure bell such that a lower pressure area is created within the pressure bell thereby drawing blood to a surface of the skin of the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new apparatus for producing a hematoma apparatus and method which has many of the advantages of the localized negative pressure devices mentioned heretofore and many novel features that result in a new apparatus for producing a hematoma which is not anticipated, rendered obvious, suggested, or even implied by any of the prior art localized negative pressure devices, either alone or in any combination thereof.

It is another object of the present invention to provide a new apparatus for producing a hematoma which may be easily and efficiently manufactured and marketed.

It is a further object of the present invention to provide a new apparatus for producing a hematoma which is of a durable and reliable construction.

An even further object of the present invention is to provide a new apparatus for producing a hematoma which is susceptible of a low cost of manufacture with regard to both materials and labor, and which accordingly is then susceptible of low prices of sale to the consuming public, thereby making such apparatus for producing a hematoma economically available to the buying public.

Still yet another object of the present invention is to provide a new apparatus for producing a hematoma which provides in the apparatuses and methods of the prior art some of the advantages thereof, while simultaneously overcoming some of the disadvantages normally associated therewith.

Still another object of the present invention is to provide a new apparatus for producing a hematoma for encouraging the increased production of hemoglobin.

Yet another object of the present invention is to provide a new apparatus for producing a hematoma which includes a pressure bell having a wall defining an interior space and a lip extending around a lower periphery of the wall designed for providing a substantially airtight seal against a skin of a user, a housing removably coupled to and in fluid communication with an insertion port of the pressure bell, and a vacuum assembly positioned within the housing for removing air from the interior space of the pressure bell such that a lower pressure area is created within the pressure bell thereby drawing blood to a surface of the skin of the user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
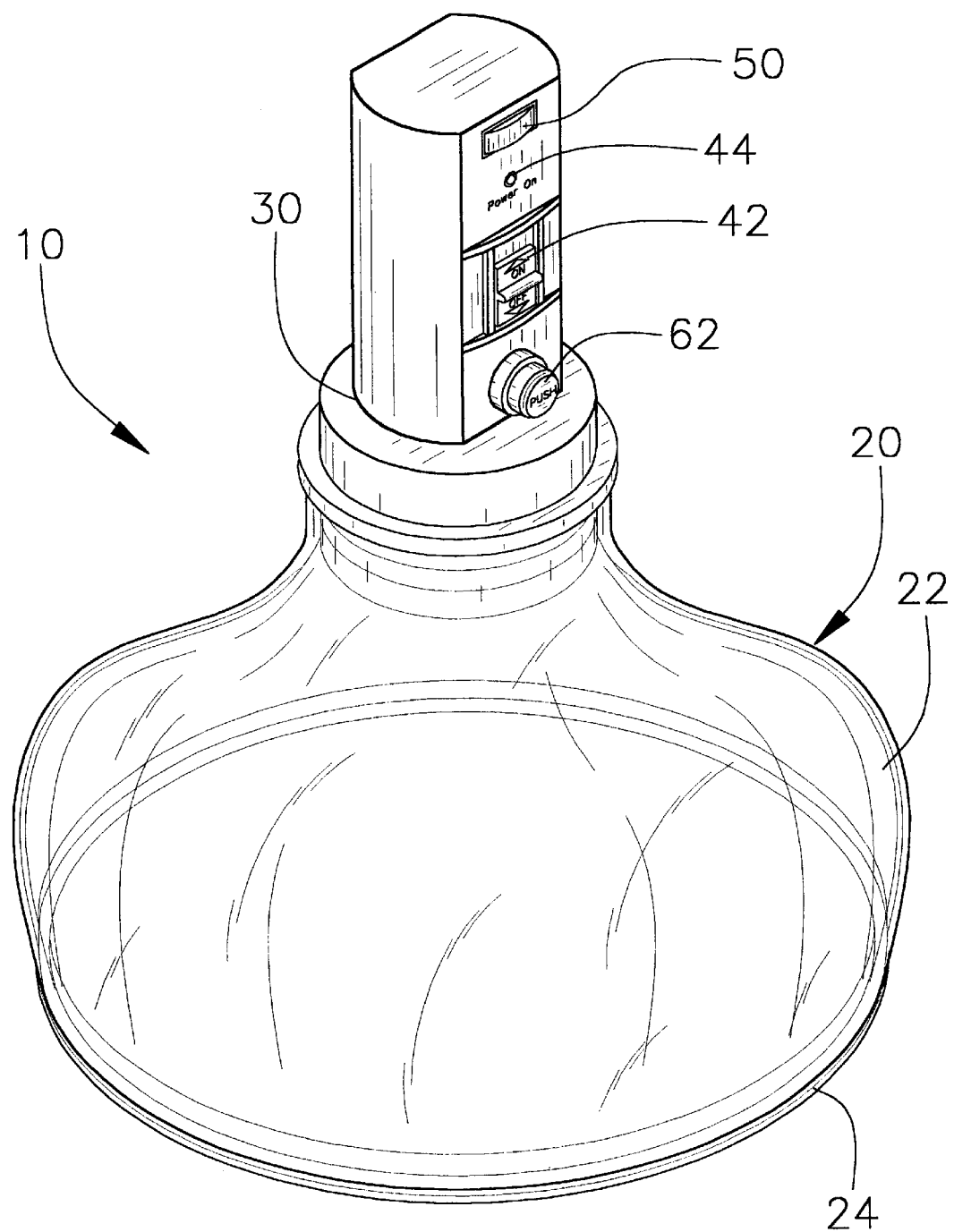
FIG. 1 is a schematic perspective view of a new apparatus for producing a hematoma according to the present invention.
Figure 2:
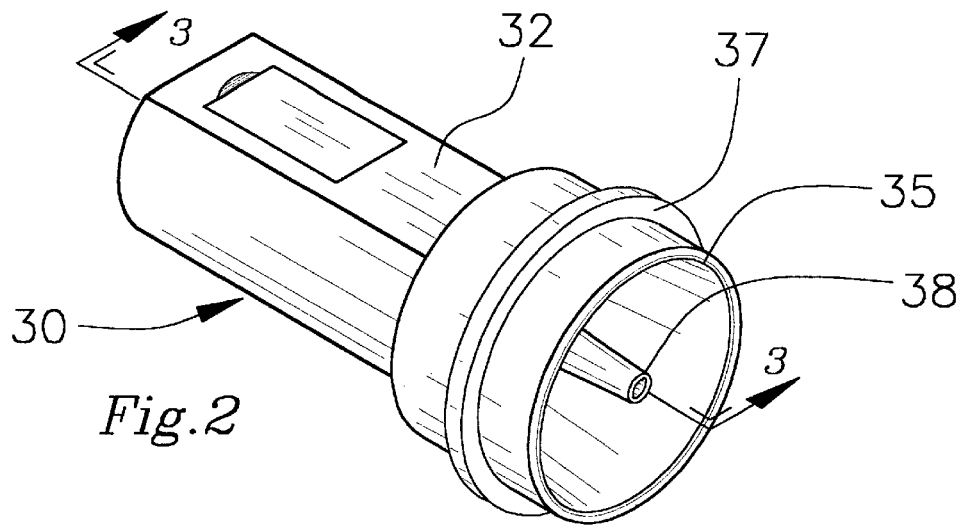
FIG. 2 is a schematic perspective view of the housing of the present invention.
Figure 3:
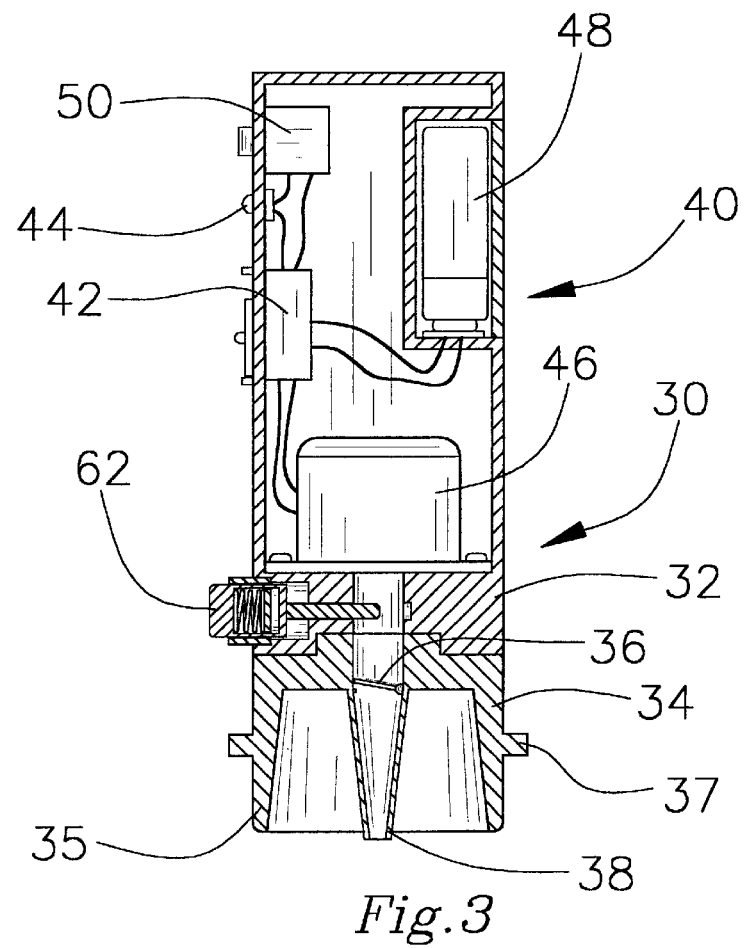
FIG. 3 is a schematic cross-sectional view of the present invention taken along line 3—3 of FIG. 2.
Figure 4:
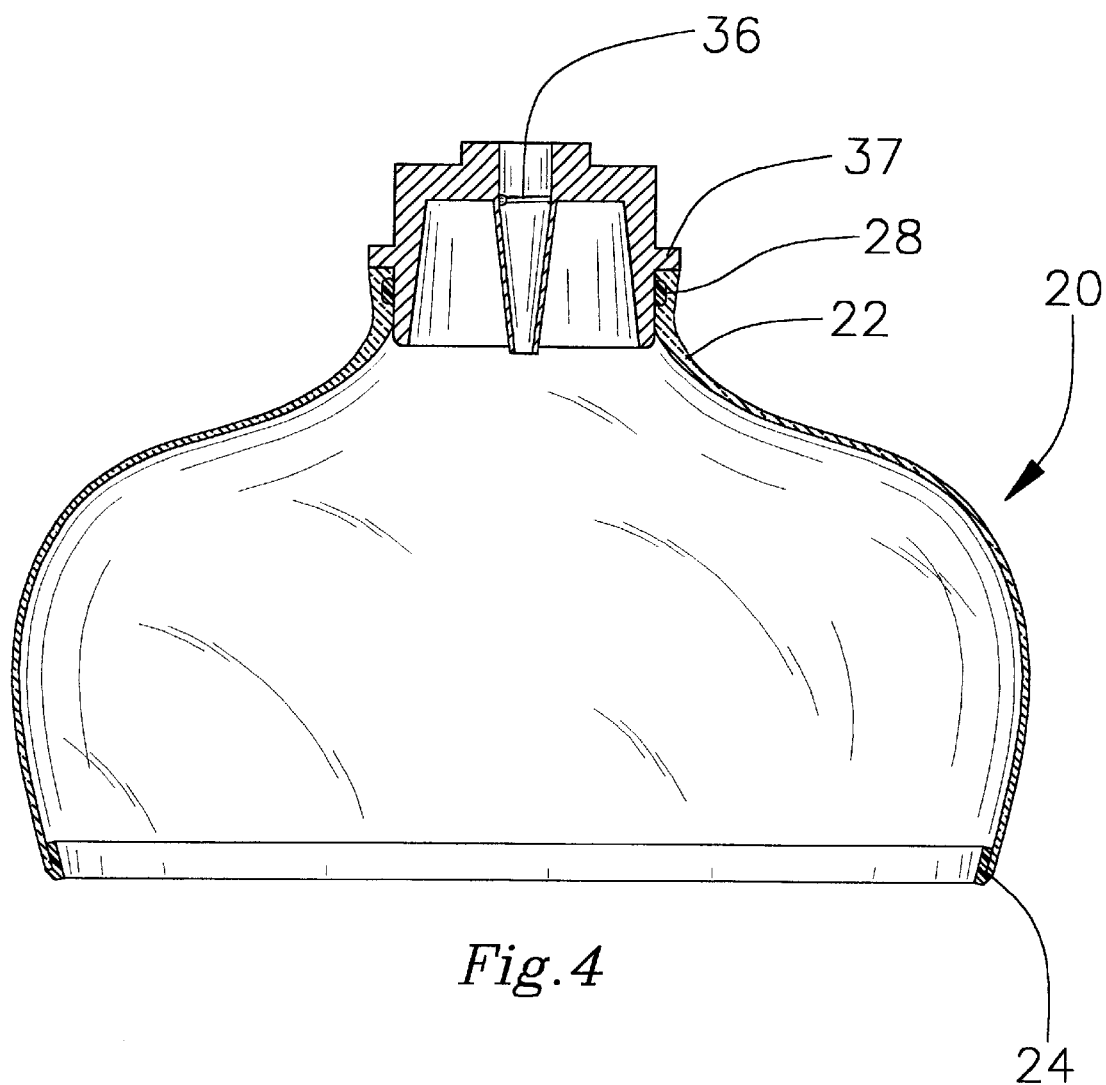
FIG. 4 is a schematic cross-sectional view of the pressure bell of the present invention.

With reference now to the drawings, and in particular to FIGS. 1 through 4 thereof, a new apparatus for producing a hematoma embodying the principles and concepts of the present invention and generally designated by the reference numeral 10 will be described.

As best illustrated in FIGS. 1 through 4, the apparatus for producing a hematoma 10 generally comprises a pressure bell 20, a housing 30, a pressure equalization assembly 60, and a pressure switch 62.

The pressure bell 20 includes a wall 22. The wall 22 defines an interior space. The pressure bell 20 includes a lip 24, which extends around a lower periphery of the wall 22 of the pressure bell 20 such that the lip 24 of the pressure bell 20 is designed for providing a substantially airtight seal against a skin of a user.

The housing 30 includes a vacuum assembly 40 within the housing 30. The vacuum housing 30 is removably coupled to an insertion port 26 of the pressure bell 20. The vacuum assembly 40 is in fluid communication with the interior space of the pressure bell 20. The vacuum assembly 40 is used for removing air within the interior space of the pressure bell 20 such that the vacuum assembly 40 creates a lower pressure area within the interior space of the pressure bell 20 thereby drawing blood to a surface of the skin of the user.

In an embodiment the vacuum assembly 40 has a switch 42 for actuating the vacuum assembly 40. The switch 42 being coupled to an outer surface of the housing 30 such that the housing 30 is designed for being held in a hand of the user. Thus the switch 42 may be actuated by a finger of the hand of the user.

In a further embodiment the vacuum assembly 40 has a light 44 coupled to an outer surface of the housing 30. The light 44 is for indicating actuation of the switch 42.

In yet a further embodiment the vacuum assembly 40 has a vacuum motor 46 which is in fluid communication with the interior space of the pressure bell 20. The vacuum motor 46 is for removing air from the pressure bell 20 to create the low pressure area within the interior space of the pressure bell 20. The switch 42 is operationally coupled to the vacuum motor 46 such that the switch 42 is for actuating the vacuum motor 46. The vacuum motor 46 is positioned within the housing 30.

In still a further embodiment the vacuum assembly 40 has a power supply 48 operationally coupled to the switch 42. The power supply 48 provides electricity to the vacuum motor 46.

In an even further embodiment the vacuum assembly 40 has a pressure gauge 50 coupled to the outer surface of the housing 30 such that the pressure gauge 50 is designed for being viewed by the user. The pressure gauge 50 is operationally coupled to the vacuum motor 46 such that the pressure gauge 50 is for measuring pressure created by the vacuum motor 46 in the interior space of the pressure bell 20.

In an embodiment the housing 30 has main portion 32 and a interface portion 34 removably coupleable to the main portion 32 of the housing 30. The interface portion 34 of the housing 30 is removably coupleable to the insertion port 26 of the pressure bell 20.

In a further embodiment the interface portion 34 of the housing 30 has a valve 36 positioned within a bore of the interface portion 34. The valve 36 is for preventing equalization of pressure within the interior space of the pressure bell 20 when the lower pressure area has been created within the interior space of the pressure bell 20 by the vacuum assembly 40.

In still a further embodiment the main portion 32 of the housing 30 has an aperture 38, which extends through a lower surface of the main portion 32 of the housing 30. The aperture 38 is in fluid communication with the vacuum motor 46. The aperture 38 of the main portion 32 is aligned with the bore of interface portion 34 when the main portion 32 is coupled to the interface portion 34.

In yet a further embodiment the interface portion 34 has a peripheral wall 35 for engaging the insertion port 36 of the pressure bell 20. An annular ring 37 extends outwardly from the peripheral wall 35 of the interface portion 34 such that the annular ring 37 abuts an upper edge of the insertion port 26 of the pressure bell 20.

In still yet a further embodiment the insertion port 26 of the pressure bell 20 has a seal 28 for engaging the peripheral wall 35 of the interface portion 34 of the housing 30 such that the seal 28 provides an airtight seal between the insertion port 26 of the pressure bell 20 and the interface portion 34 of the housing 30.

The pressure equalization assembly 60 is for equalizing pressure within the interior space of the pressure bell 20 with the air pressure outside of the pressure bell 20. The pressure equalization assembly 60 is coupled to the housing 30 proximate to the insertion port 26 of the pressure bell 20.

The pressure switch 62 is coupled to the housing 30. The pressure switch 62 is operationally coupled to the pressure equalization assembly 60 such that actuation of the pressure switch 62 actuates the pressure equalization assembly 60.

In use, the user selects a desired area of the body to induce a hematoma. The user then places the pressure bell over the desired area and activates the vacuum assembly by placing the switch in the on position. The vacuum motor then generates a lower pressure within the pressure bell. The user may monitor the vacuum pressure being generated by observing the pressure gauge. One the desired hematoma has been created, the user may then shut off the vacuum motor and equalize the pressure by toggling the pressure switch.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An apparatus for producing a hematoma, said apparatus comprising:
    a pressure bell having a wall, said wall defining an interior space, said pressure bell having a lip extending around a lower periphery of said wall of said pressure bell such that said lip of said pressure bell is designed for providing a substantially airtight seal against a skin of a user;
    a housing having a vacuum assembly within said housing, said vacuum housing being removably coupled to an insertion port of said pressure bell, said vacuum assembly being in fluid communication with said interior space of said pressure bell, said vacuum assembly for removing air within said interior space of said pressure bell such that said vacuum assembly creates a lower pressure area within said interior space of said pressure bell thereby drawing blood to a surface of the skin of the user;
    said housing having main portion and a interface portion being removably coupleable to said main portion of said housing, said interface portion of said housing being removably coupleable to said insertion port of said pressure bell; and
    said interface portion having a peripheral wall being for engaging said insertion port of said pressure bell, an annular ring extending outwardly from said peripheral wall of said interface portion such that said annular ring abuts an upper edge of said insertion port of said pressure bell.

2. The apparatus as set forth in claim 1, wherein said vacuum assembly has a switch for actuating said vacuum assembly, said switch being coupled to an outer surface of said housing such that said housing is designed for being held in a hand of the user whereby said switch may be actuated by a finger of the hand of the user.

3. The apparatus as set forth in claim 2, wherein said vacuum assembly has a light coupled to an outer surface of said housing, said light being for indicating actuation of said switch.

4. The apparatus as set forth in claim 3, wherein said vacuum assembly has a vacuum motor being in fluid communication with said interior space of said pressure bell, said vacuum motor being for removing air from said pressure bell to create the low pressure area within said interior space of said pressure bell, said switch being operationally coupled to said vacuum motor such that said switch is for actuating said vacuum motor, said vacuum motor being positioned within said housing.

5. The apparatus as set forth in claim 3, wherein said vacuum assembly has a power supply being operationally coupled to said switch, said power supply being for providing electricity to said vacuum motor.

6. The apparatus as set forth in claim 5, wherein said vacuum assembly has a light coupled to said outer surface of said housing, said light being operationally coupled to said switch, said light being lit when said switch is actuated.

7. The apparatus as set forth in claim 5, wherein said vacuum assembly has a pressure gauge coupled to said outer surface of said housing such that said pressure gauge is designed for being viewed by the user, said pressure gauge being operationally coupled to said vacuum motor such that said pressure gauge is for measuring pressure created by said vacuum motor in said interior space of said pressure bell.

8. The apparatus as set forth in claim 1, wherein said interface portion of said housing has a valve positioned within a bore of said interface portion, said valve being for preventing equalization of pressure within said interior space of said pressure bell when the lower pressure area has been created within said interior space of said pressure bell by said vacuum assembly.

9. The apparatus as set forth in claim 8, wherein said main portion of said housing has an aperture extending through a lower surface of said main portion of said housing, said aperture being in fluid communication with said vacuum motor, said aperture of said main portion being aligned with said bore of interface portion when said main portion is coupled to said interface portion.

10. The apparatus as set forth in claim 1, wherein said insertion port of said pressure bell has a seal for engaging said peripheral wall of said interface portion of said housing such that said seal provides an airtight seal between said insertion port of said pressure bell and said interface portion of said housing.

11. The apparatus as set forth in claim 1, further comprising:
    a pressure equalization assembly being for equalizing pressure within said interior space of said pressure bell with the air pressure outside of said pressure bell, said pressure equalization assembly being couple to said housing proximate said insertion port of said pressure bell.

12. The apparatus as set forth in claim 11, further comprising:
    a pressure switch being coupled to said housing, said pressure switch being operationally coupled to said pressure equalization assembly such that actuation of said pressure switch actuates said pressure equalization assembly.

13. An apparatus for producing a hematoma, said apparatus comprising:
- a pressure bell having a wall, said wall defining an interior space, said pressure bell having a lip extending around a lower periphery of said wall of said pressure bell such that said lip of said pressure bell is designed for providing a substantially airtight seal against a skin of a user;
- a housing having a vacuum assembly within said housing, said vacuum housing being removably coupled to an insertion port of said pressure bell, said vacuum assembly being in fluid communication with said interior space of said pressure bell, said vacuum assembly for removing air within said interior space of said pressure bell such that said vacuum assembly creates a lower pressure area within said interior space of said pressure bell thereby drawing blood to a surface of the skin of the user;
- wherein said vacuum assembly has a switch for actuating said vacuum assembly, said switch being coupled to an outer surface of said housing such that said housing is designed for being held in a hand of the user whereby said switch may be actuated by a finger of the hand of the user;
- wherein said vacuum assembly has a light coupled to an outer surface of said housing, said light being for indicating actuation of said switch;
- wherein said vacuum assembly has a vacuum motor being in fluid communication with said interior space of said pressure bell, said vacuum motor being for removing air from said pressure bell to create the low pressure area within said interior space of said pressure bell, said switch being operationally coupled to said vacuum motor such that said switch is for actuating said vacuum motor, said vacuum motor being positioned within said housing;
- wherein said vacuum assembly has a power supply being operationally coupled to said switch, said power supply being for providing electricity to said vacuum motor;
- wherein said vacuum assembly has a light coupled to said outer surface of said housing, said light being operationally coupled to said switch, said light being lit when said switch is actuated;
- wherein said vacuum assembly has a pressure gauge coupled to said outer surface of said housing such that said pressure gauge is designed for being viewed by the user, said pressure gauge being operationally coupled to said vacuum motor such that said pressure gauge is for measuring pressure created by said vacuum motor in said interior space of said pressure bell;
- wherein said housing has main portion and a interface portion being removably coupleable to said main portion of said housing, said interface portion of said housing being removably coupleable to said insertion port of said pressure bell;
- wherein said interface portion of said housing has a valve positioned within a bore of said interface portion, said valve being for preventing equalization of pressure within said interior space of said pressure bell when the lower pressure area has been created within said interior space of said pressure bell by said vacuum assembly;
- wherein said main portion of said housing has an aperture extending through a lower surface of said main portion of said housing, said aperture being in fluid communication with said vacuum motor, said aperture of said main portion being aligned with said bore of interface portion when said main portion is coupled to said interface portion;
- wherein said interface portion has a peripheral wall being for engaging said insertion port of said pressure bell, an annular ring extending outwardly from said peripheral wall of said interface portion such that said annular ring abuts an upper edge of said insertion port of said pressure bell,
- wherein said insertion port of said pressure bell has a seal for engaging said peripheral wall of said interface portion of said housing such that said seal provides an airtight seal between said insertion port of said pressure bell and said interface portion of said housing;
- a pressure equalization assembly being for equalizing pressure within said interior space of said pressure bell with the air pressure outside of said pressure bell, said pressure equalization assembly being couple to said housing proximate said insertion port of said pressure bell; and
- a pressure switch being coupled to said housing, said pressure switch being operationally coupled to said pressure equalization assembly such that actuation of said pressure switch actuates said pressure equalization assembly.

* * * * *